United States Patent [19]

Jennings

[11] Patent Number: 5,552,113
[45] Date of Patent: Sep. 3, 1996

[54] AUTOCLAVE

[76] Inventor: Stanley C. Jennings, Kismet, Bridge Hill, Epping Essex CM16 4ER, United Kingdom

[21] Appl. No.: 275,775

[22] Filed: Jul. 15, 1994

[30] Foreign Application Priority Data

Jul. 16, 1993 [GB] United Kingdom .................. 9314761

[51] Int. Cl.⁶ ..................................................... A61L 2/06
[52] U.S. Cl. .............................. 422/26; 422/297; 422/299
[58] Field of Search .................................. 422/26, 29, 33, 422/297, 298, 299, 300, 303, 307, 295

[56] References Cited

U.S. PATENT DOCUMENTS

| | | | |
|---|---|---|---|
| 1,217,113 | 2/1917 | Darnall | 422/295 |
| 2,162,228 | 6/1939 | Peirce | 422/303 |
| 2,340,206 | 1/1944 | Richards | 422/300 |
| 3,811,408 | 5/1974 | Thompson | 134/99.1 X |
| 4,400,357 | 8/1983 | Hohmann | 422/299 X |
| 4,544,529 | 10/1985 | Hoeck | 422/298 X |
| 4,663,122 | 5/1987 | Sparks | 422/26 |
| 4,752,444 | 6/1988 | Bowen et al. | 422/28 |
| 5,057,283 | 10/1991 | Guggenheim et al. | 422/292 |
| 5,120,512 | 6/1992 | Masuda | 422/295 |
| 5,137,689 | 8/1992 | Cantrell | 422/300 |
| 5,290,511 | 3/1994 | Newman | 422/26 |
| 5,326,492 | 7/1994 | Hodam, Jr. | 252/106 |
| 5,348,711 | 9/1994 | Johnson et al. | 422/300 |

FOREIGN PATENT DOCUMENTS 2035278  6/1980  United Kingdom .................. 422/303

*Primary Examiner*—Robert J. Warden
*Assistant Examiner*—Theresa T. Snider
*Attorney, Agent, or Firm*—William Lloyd Clayborn; John M. Cone

[57] ABSTRACT

An autoclave (1) for sterilizing at least one generally hollow article having openings at remote ends thereof, such as a dental drill handpiece (21), includes an article carrier (17) and at least one adaptor (20) for passing dry saturated steam through the article to sterilize the interior thereof.

13 Claims, 2 Drawing Sheets

AUTOCLAVE

FIELD OF THE INVENTION

This invention relates to an autoclave and an associated method of sterilizing generally hollow, and preferably generally tubular, articles with openings at remote ends thereof. The invention is especially, but not exclusively, related to the sterilization of handpieces for dental drills.

DESCRIPTION OF THE PRIOR ART

Known autoclaves for sterilizing handpieces for dental drills comprise a closed chamber through which dry saturated steam can be passed or circulated and in which one or more trays of handpieces to be sterilized can be stacked. During sterilization, the dry saturated steam is supposed to sterilize all of the surfaces of the handpieces which have be exposed to contamination during use. However, because the pressure of the steam is the same at both open ends of the generally hollow handpieces, little, if any, sterilizing steam is able to pass into and through the handpieces, such that the hollow interiors thereof are not sterilized properly. This may well result in contamination and/or infection of a patient upon whom an improperly sterilized handpiece is used subsequently.

Further, particles of tissue and broken tooth can become clogged inside the hollow interiors of the handpieces, whereby use of known types of autoclave is not capable of dislodging such foreign matter, thus resulting in an undesirable build-up of such matter inside the handpieces, with consequential contamination and/or infection of patients upon whom the supposedly cleaned and sterilized handpieces are used.

SUMMARY OF THE INVENTION

It is an object of the present invention to provide an autoclave which overcomes or at least substantially reduces the serious disadvantages associated with known types of autoclave, such as those discussed above.

It is another object of the invention to provide a method of sterilizing generally open-ended, hollow articles, such as, handpieces for dental drills, which also overcomes or at least substantially reduces the disadvantages of known sterilizing techniques.

Accordingly, one aspect of the invention resides in an autoclave comprising means arranged to pass a sterilizing fluid, such as, steam and, preferably, dry saturated steam, through a generally hollow article with openings at remote ends thereof, to sterilize the interior thereof.

Another aspect of the invention provides a method of sterilizing a generally hollow article with communicating openings therein, preferably at remote ends thereof, wherein a sterilizing fluid, such as, steam and preferably dry saturated steam, is passed through the article via said openings, to sterilize the interior thereof.

Preferably, the sterilizing fluid is dry saturated steam which may be passed through the hollow interior of the article to be sterilized at such a pressure as to dislodge any foreign matter therefrom.

In a preferred embodiment of the inventive autoclave, the means for passing sterilizing steam through the hollow interior of a dental drill handpiece comprises an adaptor mounted upon a carrier and arranged to lie in register with an aperture, such as, a hole or tube, passing through the carrier and in communication with a source of pressurised, dry saturated steam. A handpiece to be sterilized in the autoclave has one open end mounted upon the adaptor, such that its interior is also able to communicate with the in-register aperture in the carrier, so that steam can pass through the hollow interior of the handpiece and be expelled from the opening(s) at the other, remote end of the handpiece.

The pressure of the steam may be such that it is sufficient to dislodge any foreign matter, such as, particles of tissue and/or broken tooth, from the handpiece interior.

Also, the adaptor may be modified so that the steam pressure is sufficient also to rotate the handpiece about its longitudinal axis during sterilization. Such rotation may assist further in dislodging any foreign matter from the handpiece interior.

The adaptor can be arranged to receive different sizes of handpiece and may be connected thereto by a push-fit, screw thread or other suitable means.

When handpieces having their working heads driven by air motors, turbines or other rotating means, are to be sterilized, then the adaptor of the carrier may be such that the pressurised steam can rotate the driving air motors, turbine, or other rotating means associated with the handpiece.

Alternatively, the adaptor may be designed to rotate the handpiece about its normal air bearing in any suitable manner, for example, by being rotated itself such that the handpiece which is fixed thereto is also rotated. However, other suitable means may be provided for rotating the handpiece and/or adaptor.

In order that the invention may be more fully understood, a preferred embodiment of autoclave in accordance therewith and for putting the inventive method into effect, will now be described by way of example and with reference to the accompanying drawings in which:

DETAILED DESCRIPTION OF THE PREFERRED EMBODIMENT

Figure 1:
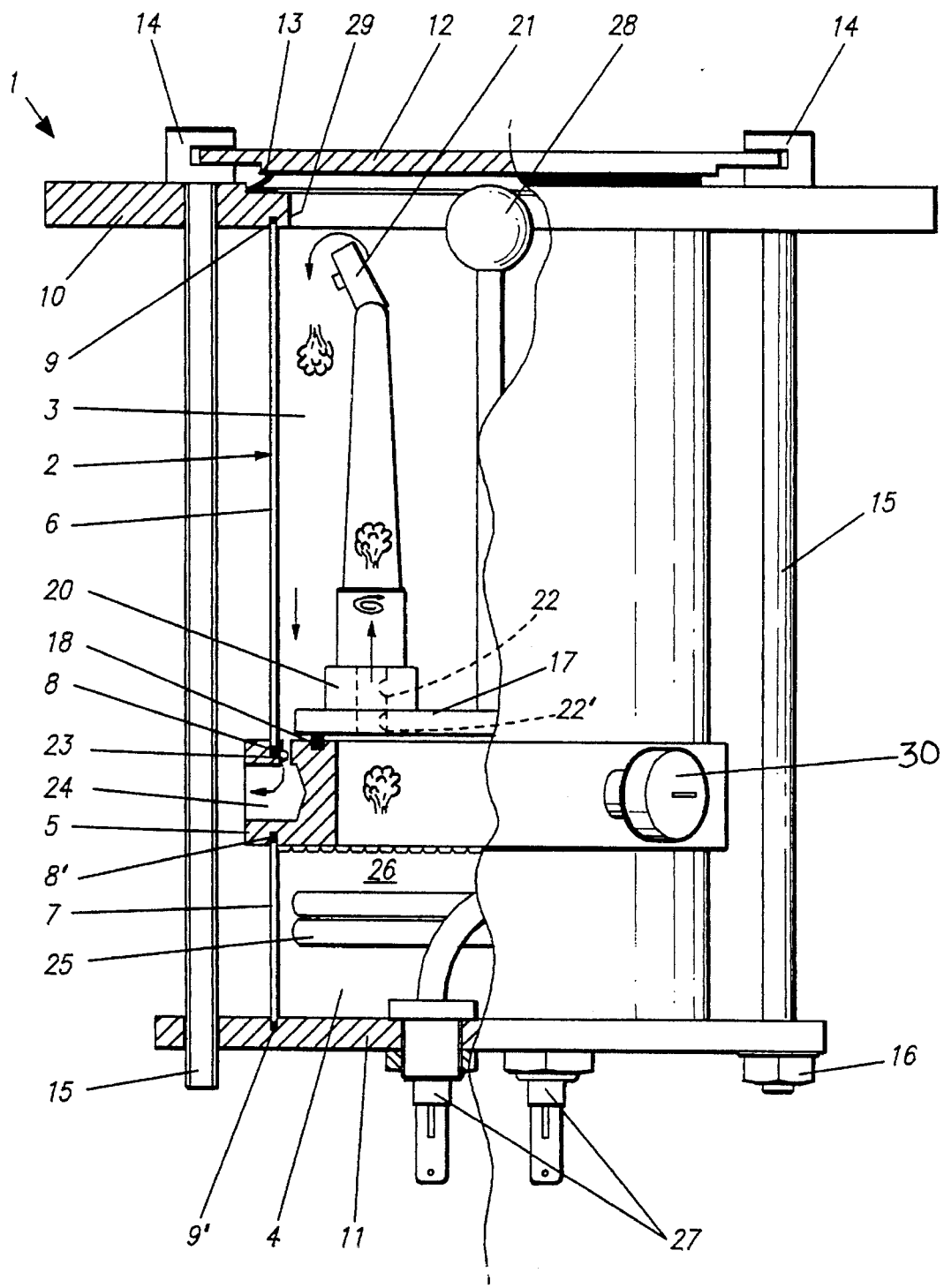
FIG. 1 is a cut-away, elevation in partial section of an autoclave for sterilizing handpieces for dental drills.
Figure 2:
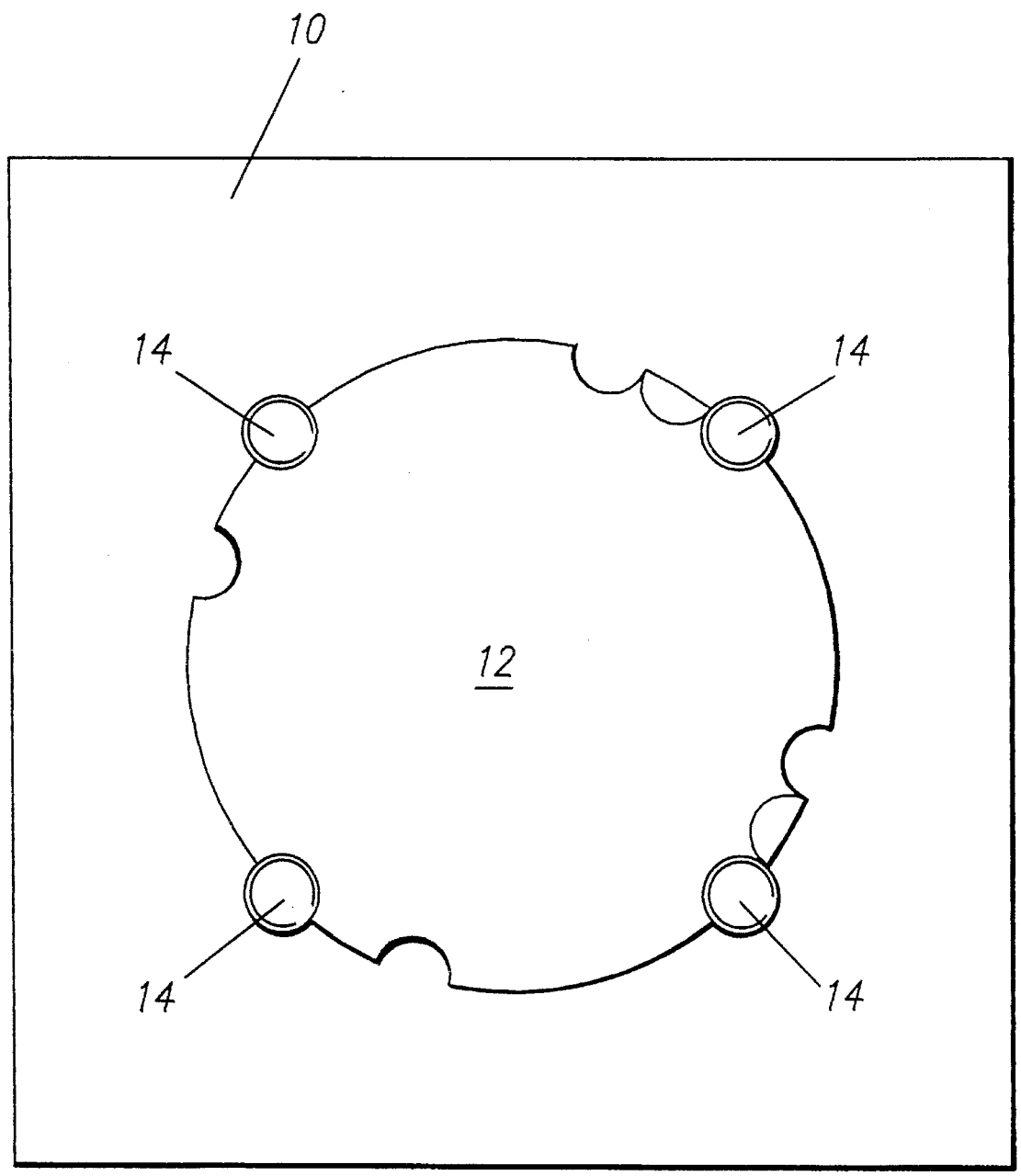
FIG. 2 is a plan view of the autoclave of FIG. 1.

Referring now to the drawings, an autoclave for sterilizing dental equipment, in particular handpieces for dental drills, is shown generally at 1 and comprises a cylindrical body 2 divided into an upper, sterilizing chamber 3 and a lower, steam-generation chamber 4 by means of an annular support 5. Respective lower and upper ends of upper and lower cylindrical wall portions 6,7 of the body 2 engage sealingly with the annular support 5 by means of seals 8,8'. Similarly, the respective upper and lower ends of those wall portions 6,7 engage sealingly with top and base plates 10 and 11 by means of seals 9,9'. A lid 12 is sealed to the top plate 10 via an annular lip 13 and is located in position by means of four fixing studs 14 situated at the top ends of respective clamping rods 15 which, in combination with retaining nuts 16 (only one shown), clamp the autoclave assembly together.

Mounted on the support 5 in the upper, sterilizing chamber 3 is a circular carrier 17 resting upon another seal 18 located in an annular groove in the support 5. A plurality of adaptors 20 (only one shown) are arranged on the upper surface of the carrier 17 for receiving thereon respective handpieces 21 for dental drills (not shown). The handpieces 21 are generally tubular and hollow and each have an open end, in this case, the lower end, and the opposed end provided with openings dependent upon their particular construction. An axial bore 22 in each adaptor 20 lies in register with a corresponding aperture 22', or tube as an alternative, passing through the carrier 17, such that the hollow interior of the handpiece 21 is in communication with the lower, steam-generation chamber 4, via the large central aperture of the annular support 5. The other, upper end of the handpiece 21 is in communication with the interior of the upper, sterilizing chamber 3 via the openings in that end of the handpiece 21. In turn, the sterilizing chamber 3 communicates with the atmosphere via a hole 23 and an exhaust port 24 in the support 5. The hole 23 or the exhaust port 24 may be provided with a bleed valve, as will be mentioned hereinbelow.

A heating element 25 is provided in the lower chamber 4 for heating water 26 contained therein, with associated electric terminals 27 located on the underside of the base plate 11. Also, the carrier 17 has a handle 28 for maneuvering the carrier, and any handpieces 21 mounted thereon, in and out of the sterilizing chamber 3.

The lid 12 is removable, whilst the carrier 17 is dimensioned so that it can be passed through the circular central aperture 29 in the top plate 10, with the lid removed.

Further, the handpieces 21 are, in use with a dental drill, air driven and the adaptors 20 are such that, when a handpiece is mounted upon one, as shown in FIG. 1, and steam is generated in the lower chamber 4, steam passing through the hollow interior of the handpiece 21 is at a sufficient pressure to rotate the air motor or turbine of the handpiece or the handpiece itself during sterilization thereof. Such rotation assists in dislodging any foreign matter, such as, particles of tissue and/or broken tooth, from the interior of the handpiece, which matter might not otherwise be dislodged by conventional sterilizing techniques.

A pressure relief valve 30 for the lower chamber 4 is also provided in association with the support 5, for emergency purposes.

In use of the inventive autoclave 1 described above in relation to the drawings, the carrier 17 bearing one or more handpieces 21 mounted on associated adaptors 20 is placed in the upper chamber 3, and seated upon the seal 18 of the support to provide a steam-tight seal between the upper and lower chambers 3,4. The lid 12 is then secured in position using the fixing studs 14.

Then, the lower chamber 4 is filled to a given level with water 26 and the heating element 25 is switched on. As the water 26 boils, the pressure in the lower chamber 4 increases to provide dry saturated steam at a temperature of, say, 134° C.

Because the pressure of the steam in the lower chamber 4 is greater than the pressure in the upper chamber 3, the dry saturated steam passes through each aperture or tube 22' in the carrier 17 and each corresponding in-register bore 22 of each adaptor 20, so that the steam eventually passes through the hollow interior of each handpiece 21 and into the upper chamber 3, via the openings in the upper end of each handpiece, where it sterilizes the outer surfaces of the handpiece 21.

Passage of the dry saturated steam through the hollow interior of each handpiece 21 not only sterilizes the interior of each handpiece 21 but also assists in dislodging any foreign matter which may have built-up inside the handpieces 21.

Further, the pressure of the steam, and hence its rate of flow through the interiors of the handpieces 21, is sufficient to rotate the handpieces upon their respective adaptors 20 or the air motors or turbines for driving the working heads of the handpieces 21.

The steam pressure generated within the upper chamber 3 during normal use of the autoclave 1 will be about two atmospheres, although other steam pressures are acceptable, depending upon particular operating conditions. Similarly, the suggested dry saturated steam temperature of 134° C. can also be varied, again depending upon operating conditions.

A predetermined sterilizing cycle time for the autoclave 1 can be provided in dependence upon a leakage setting of a bleed valve (not shown) associated with the hole 23 and/or steam exhaust port 24, a given amount of water contained in the lower chamber 4 and a given temperature and pressure of the dry saturated steam.

The adaptors 20 can be arranged to receive different sizes of handpiece 21 and may be connectable thereto by a push-fit, screw thread or any other suitable means.

I claim:

1. An autoclave for sterilizing generally hollow articles having a first end opening and a second opening remote from the first end opening, the autoclave comprising:

a substantially sealed chamber to facilitate operation at greater than atmospheric pressure;

a steam generator disposed within the chamber and capable of generating dry saturated steam;

an article carrier mountable on the steam generator in sealing engagement; and at least one adaptor for receiving steam from the steam generator, the adaptor being attached to the carrier and in fluid communication with the steam generator;

the adaptor being constructed to sealingly mount a generally hollow article to be sterilized at the first end opening thereof;

whereby steam from the steam generator may pass into, through, and out of the generally hollow article at the second opening.

2. The autoclave of claim 1 wherein the steam generator is constructed to generate steam at such a pressure as to cause the steam to pass through the generally hollow article at a pressure sufficient to dislodge foreign matter therefrom.

3. The autoclave of claim 1, wherein the adaptor is mounted upon the carrier to lie in register with an aperture in the carrier, said aperture passing through the carrier and communicating with the steam generator, the adaptor being such that, in use, a generally hollow article to be sterilized may have the first end opening thereof sealingly mounted upon the adaptor.

4. The autoclave of claim 3, wherein the adaptor is constructed to receive differently-sized generally hollow articles.

5. The autoclave of claim 3, wherein the adaptor is constructed to offer one of a push-fit and a screw-threaded connection with the generally hollow article mountable thereon.

6. The autoclave of claim 3, wherein, for sterilizing air-driven dental handpieces, the adaptor is constructed to deliver pressurized steam to the handpiece at sufficient pressure to rotate an air motor or turbine associated therewith.

7. The autoclave of claim 3, wherein the adaptor is rotably mounted on the carrier, so that, in use, the generally hollow article mounted thereon will rotate about an axis of the generally hollow article.

8. A method for sterilizing a generally hollow article having a first end opening and a second opening remote from the first end opening, the method comprising:

a. providing a substantially sealed chamber to facilitate operation at greater than atmospheric pressure;

b. providing a steam generator disposed within the chamber and capable of generating dry saturated steam;

c. sealingly mounting a generally hollow article having a first end opening and a second opening remote from the first end opening by the first end opening to an adaptor;

d. supplying dry saturated steam from the steam generator to the interior of the article via the adaptor so as to cause the steam to pass through and out of the article at the second opening and into the chamber, thereby sterilizing said article.

9. The method of claim 8, wherein the steam is passed through the interior of the article at such a pressure as to dislodge foreign matter therefrom.

10. The method of claim 8, wherein the generally hollow article is a dental drill handpiece.

11. The method of claim 10, wherein the adaptor is rotatable and the steam pressure passing therethrough rotates the adaptor, thereby rotating the handpiece about an axis during sterilization thereof.

12. A method of claim 10, wherein the handpiece is mounted to the adaptor by a push-fit or screw thread.

13. The method of claim 10, wherein the generally hollow article is an air-driven, dental drill handpiece, and wherein the steam generator supplies pressurized steam which rotates an air motor or turbine associated with the handpiece.

\* \* \* \* \*